(12) United States Patent
Spits et al.

(10) Patent No.: US 8,318,487 B2
(45) Date of Patent: Nov. 27, 2012

(54) MATERIALS AND METHODS RELATING TO THE PRODUCTION AND MAINTENANCE OF CELL LINES

(75) Inventors: Hergen Spits, Amsterdam (NL); Marianne Naspetti, Marseilles (FR); Ferenc Scheeren, Amsterdam (NL); Bianca Blom, Amstelhoek (NL)

(73) Assignee: Cancer Research Technology Limited, London (GB)

( * ) Notice: Subject to any disclaimer, the term of this patent is extended or adjusted under 35 U.S.C. 154(b) by 990 days.

(21) Appl. No.: 10/499,242

(22) PCT Filed: Dec. 18, 2002

(86) PCT No.: PCT/GB02/05753
§ 371 (c)(1), (2), (4) Date: Jan. 25, 2006

(87) PCT Pub. No.: WO03/052083
PCT Pub. Date: Jun. 26, 2003

(65) Prior Publication Data
US 2006/0153820 A1    Jul. 13, 2006

(30) Foreign Application Priority Data

Dec. 18, 2001 (GB) .................................. 0130223.1
Mar. 14, 2002 (GB) .................................. 0206086.1

(51) Int. Cl.
*C12N 5/0781*  (2010.01)
*C12N 15/63*   (2006.01)
*C12N 15/64*   (2006.01)

(52) U.S. Cl. ......................... 435/375; 435/455; 435/326
(58) Field of Classification Search .................. 435/375, 435/455, 326
See application file for complete search history.

(56) References Cited

U.S. PATENT DOCUMENTS
2002/0090692 A1* 7/2002 Prayaga et al. ............... 435/183

FOREIGN PATENT DOCUMENTS
EP          0 773 228 A1    10/1996
WO         WO 95/29935      11/1995

OTHER PUBLICATIONS

Ariyoshi et al. J. Biol. Chem. 275(32):24407-24413; 2000.*
Nosaka et al. EMBO J. 18(17):4754-4765; 1999.*
Friedrich et al. Intl. Immunol. 11(8):1283-1293; 1999.*
Franzrahe, S. et al. "Establishment of Inducible Expression Systems to Study the Role of Stat-Transcription Factors in AML"; Blood, 96(11) Part 2: 132b (2000) [Abstract #4262].
Berchtold, S. et al. "Cytokine Receptor-independent, Constitutively Active Variants of STAT5"; Journal of Biological Chemistry, 272(48): 30237-30243 (1997).
Nosaka, T. et al. "STAT5 as a molecular regulator of proliferation, differentiation and apoptosis in hematopoietic cells"; EMBO, 18(17): 4754-4765 (1999).
Fearon, D. et al. "Arrested Differentiation, the Self-Renewing Memory Lymphocyte, and Vaccination"; Science, 293(5528): 248-250 (2001).
Karpas, A. et al. "A human myeloma cell line suitable for the generation of human monoclonal antibodies"; PNAS, 98(4): 1799-1804 (2001).
Kurata, H. et al. "Ectopic Expression of Activated Stat6 Induces the Expression of Th2-Specific Cytokines and Transcription Factors ... Th1 Cells"; Immunity, 11: 677-688 (1999).
O'Shea, J. "Jaks, STATs, Cytokine Signal Transduction, and Immunoregulation: Are We There Yet?"; Immunity, 7: 1-11 (1997).
Reljic, R. et al. "Suppression of Signal Transducer and Activator of Transcription 3-dependent B Lymphocyte . . . "; J. Exp. Med., 192(12): 1841-1847 (2000).
Shvarts, A. et al. "A senscence rescue screen identifies BCL6 as an inhibitor of anti-proliferatve p19ARF-p53 signaling"; Genes & Development, 16: 681-686 (2002).
Onishi, M. et al. "Identification and Characterization of a Constitutively Active STAT5 Mutant That Promotes Cell . . . "; Molecular and Cell Biol, 18(7): 3871-3879 (1998).
Harris, M.B. et al. "Transcriptional Repression of Stat6-Dependent Interleukin-4-Induced Genes by BCL-6: . . . "; Molecular and Cellular Biol., 19(10): 7264-7275 (1999).
Friedrich, K., et al., "Activation of STAT5 by IL-4 relies on Janus kinase function but not on receptor tyrosine phosphorylation . . . ", Int. Immunol., 11(8):1283-1293, (1999).
Frank, D.A., et al., "BCR/abl leads to the constitutive activation of Stat proteins, and shares an epitope with tyrosine . . . ", Leukemia, 10:1724-1730, (1996).
van der Plas, D.C., et al., "Interleukin-7 signaling in human B cell precursor acute lymphoblastic leukemia cells and murine BAF3 . . . ", Leukemia, 10:1317-1325, (1996).
Ariyoshi, K., et al., "Constitutive activation of STAT5 by a point mutation in the SH2 domain", J. Biol. Chem., 275(32):24407-24413, (2000).
Matsumura, I., et al., "Transcriptional regulation of the cyclin D1 promoter by STAT5: its involvement in cytokine-dependent . . . ", EMBO J., 18(5):1367-1377, (1999).
Spiekermann, K., et al., "Constitutive activation of STAT transcription factors in acute myelogenous leukemia", Eur. J. Haematol., 67:63-71, (2001).
Mizuguchi, R., et al. "Ras and Signal Transducer and Activator of Transcription (STAT) Are Essential and Sufficient Downstream Components of Janus Kinases in Cell Proliferation." Japanese Journal of Cancer Research, 91: 527-533 (May 2000). Sasaki, Y. "Cytokine Receptor Signal Transduction." Journal of Clinical and Experimental Medicine, 193(10): 854-858 (Jun. 3, 2000). [English Translation].
Sexl, V., et al. "Stat5a/b contribute to interleukin 7-induced B-cell precursor expansion, but abl-and bcr/abl-induced transformation are independent of stat5." Blood. Sep 15, 2000;96(6):2277-83.
Maru, Y. "Molecular biology of chronic myeloid leukemia." Int J Hematol. Apr. 2001;73(3):308-22.

* cited by examiner

*Primary Examiner* — Anne Marie S Wehbe
(74) *Attorney, Agent, or Firm* — Dann Dorfman Herrell & Skillman; Kathleen D. Rigaut (57) ABSTRACT

The invention provides methods for maintaining cell lines from primary cells, i.e. non-transformed cells, using expression of the signal transducer of activation and transcription (STAT). The methods are particularly suitable for the maintenance of B-cells.

9 Claims, 6 Drawing Sheets

MATERIALS AND METHODS RELATING TO THE PRODUCTION AND MAINTENANCE OF CELL LINES

This application is a §371 application of PCT/GB02/05753, filed Dec. 18, 2002, which in turn claims priority to GB Application 0130223.1, filed Dec. 18, 2001, and GB Application 0206086.1, filed Mar. 14, 2002. The entire disclosure of each of the above identified applications is incorporated by reference herein.

The field of the present invention is the production and maintenance of cell lines especially cell lines from primary cells, i.e. non-transformed cells. Particularly, but not exclusively, the present invention concerns materials and methods relating the production and maintenance of antibody producing human B cells.

Monoclonal antibodies (mAbs) are powerful tools with proven usefulness in all areas of biomedical research. The vast majority of monoclonal antibodies produced until recently have been of mouse origin. However, the application of these mAbs for therapeutic purposes in man is hampered by the fact that humans rapidly develop anti mouse antibodies when treated with mAbs of mouse origin. These immune responses against mouse mAbs strongly diminish their therapeutic efficiencies. It is therefore not surprising that extensive efforts have been undertaken to develop methods that allow the production of human monoclonal antibodies for therapeutic purposes. One strategy to achieve this goal have been to genetically re-engineer murine antibodies by exchanging constant murine antibody gene segments for their human counterparts (Jones et al., 1986; Morrison et al., 1984) or more recently to create mice carrying human Ig genes (Fishwild et al., 1996; Mendez et al., 1997). Another one is the use of phage display to create human antibodies (Hoogenboom and Chames, 2000; Winter et al., 1994). Although the value of these technologies is indisputable, it would be highly desirable to develop technology to isolate B cells producing antibodies with a wanted specificity from humans.

Specifically, the isolation of antibody-producing B cells from humans that have resolved a pathogenic challenge with high or exceptional efficiency would offer a means for the direct isolation of mAbs with proven effectiveness in a clinical setting Hybridoma-based strategies to accomplish this goal have been hampered by the problems to achieve stable fusions of human B cells with human or mouse myeloma cell lines, although a new human myeloma cell line was recently described that apparently is suitable for stable fusion with human B cells (Karpas et al., 2001). As an alternative approach antibody-producing B cells have been immortalized with Epstein Barr virus (EBV). However, these attempts have met with limited success. Although EBV-LCL clones have been established that produce antibody, the titers are low and these lines are frequently not stable (Roder et al., 1986). Moreover, EBV does not preferentially transforms cells that produce antibody.

Human B cells can be cultured for a limited period of time with CD40L and either IL-4 alone or a combination of IL-2 and Il-4 (Banchereau et al., 1991). IL-10 can induce further growth of the cultured B cells and differentiation into high antibody-producing B cells (Malisan et al., 1996). These cultured B cells have limited replicative lifespan and after 6 weeks most of the B cells have undergone apoptosis, precluding generation of stable antibody-producing lines of human B cells.

Thus, in summary, despite considerable efforts, generation of human monoclonal antibodies by fusing these cells with human or mouse myeloma cells has been very difficult. Also attempts to generate high titer antibody-producing EBV transformed B cells has been met with considerable problems.

The inventor has devised a method to establish long-term cultures of cells of specific interest, particularly antibody-producing human B cells. This method exploits the capacity of an active mutant of the signal transducer of activation and transcription (STAT), particularly STAT5, (5b or 5a) to confer an extended replicative lifespan STAT5b is activated by IL-2 and presumably plays a role in cell cycle progression induced by IL-2 (Moriggl et al., 1999). The inventor has surprisingly found that introduction of constitutive active (CA) mutants of STAT5a or STAT5b (CA-STAT5a and CA-STAT5b respectively) into human B cells enables the establishment of long term cultures of human B cells. The inventor has found that CA-STAT5b is particularly efficient at establishing long term cultures of human B cells. Further, the inventor has determined that expression of BCL-6, which inhibits differentiation of memory B cells into plasma cells (Reljic, 2000), is regulated by STAT5b. Following introduction of a hybrid of CA-STAT5b with a mutated estrogen receptor, long term B cell lines were obtained that proliferated in response to CD40L, IL-2 and IL-4 in a 4-hydroxytamoxifen dependent way. The inventor further demonstrate that BCL-6 transcripts are upregulated by STAT5b-ER in a hydroxytamoxifen-dependent way in the presence of the protein synthesis inhibitor cycloheximide, indicating that BCL-6 is a direct target of STAT5b. Thus, the data reveals a novel role of STAT5 in controlling differentiation of mature B cells.

It has recently been shown that introduction of BCL-6, which inhibits differentiation of memory B cells into plasma cells (Reljic, 2000), into human tonsil B cells results in a considerable extension of the replicative lifespan of these cells (Shvarts, 2002). BCL-6 encodes a transcriptional repressor, which is frequently activated by chromosomal translocation in non-Hodgkin's lymphoma (Ye, 1993; Chang, 1996; Staudt, 1999; Shaffer, 2000). The chromosomal translocations involving BCL-6 invariably affect the promoter only and leave the open reading frame of BCL-6 intact. Thus, BCL-6 translocations in non-Hodgkin's lymphomas contribute to oncogenesis by deregulating the expression of the wild type BCL-6 protein. BCL-6 is required for normal B and T cell development (Ye, 1997). It is believed that BCL-6 functions primarily in lymphocyte differentiation and in regulation of the immune response. This is based on the involvement of BCL-6 in non-Hodgkin's lymphoma, the defect in germinal center formation of BCL-6 knockout mice (Dent, 1997; Fukuda, 1997; Ye, 1997) and the finding that BCL-6 regulates a number of genes involved in lymphocyte physiology (Ye, 1997; Shaffer, 2000). Recently Fearon and colleagues demonstrated that BCL-6 prevents terminal differentiation of germinal center and memory B cells thereby preventing cell cycle arrest (Reljic, 2000; Fearon, 2001). Thus, the finding that BCL-6 expression in cultured human B cells results in a considerable extension of the life span of these cells (Shvarts, 2002) is consistent with the idea that terminal differentiation is responsible for the relatively short lifespan of B cells cultured with CD40L and cytokines. Given the important role of BCL-6 in regulation of differentiation and growth of B cells the question of how this gene is regulated is of great interest. Examination of the BCL-6 promoter revealed the presence of two STAT 5 binding sites (Ohashi, 1995) Giving the inventor the idea that STAT 5 may regulate expression of BCL-6.

At its most general, the present invention provides methods of maintaining a cell line by extending the replicative lifespan of the cells until such time as the cell are required to differentiate, thereby producing a desired expressed product, e.g. a protein, enzyme or antibody.

In a first aspect, there is provided a method of stabilizing a cell line comprising the steps of obtaining a cell of interest; introducing a constitutively active STAT protein into the cell; and maintaining said cell in an environment where it can replicate.

The STAT protein is preferably STAT5a or STAT5, more preferably STAT5a or STAT5b.

For exemplification of the present invention, the inventor has used the signal transducer of activation and transcription STAT5. However, it may be that other STATs (e.g. STAT1, 2, 3, 4 etc) will equally work in the present invention. Further, as the STAT family of transcription factors has been well researched in the art, the present invention also extends to upstream and downstream modulators of STAT in the STAT pathway.

Thus, the skilled person may well decide to modify the method of the invention to use a component of the STAT pathway if that component is known in the art to have an upstream effect on STAT or be regulated downstream of STAT such that it has the ability, determined for the first time by the inventor, to maintain cells in an environment where they can replicate.

For convenience, the following text concentrates on the situation where STAT protein/nucleic acid is used, particularly STAT 5. However, it should be understood that, as mentioned above, components of the STAT pathway, may equally be applied to the methods of the present invention, for example BCL-6.

The cell is preferably a mammalian cell and more preferably a B-cell, particularly human B-cell. When the cell is a B-cell, the cell is preferably maintained in an environment comprising one or more of the following components, IL-2, CD40L and IL-4.

The STAT5 protein is preferably introduced into the cell by transduction. In other words, a nucleic acid construct comprising nucleic acid encoding the STAT5 protein may be incorporated into the genome of the cell where it can be expressed. The introduction, which may also be generally referred to without limitation as "transfection" or "transformation", may employ any available technique. For eukaryotic cells, suitable techniques may include calcium phosphate transfection, DEAE-Dextran, electroporation, liposome-mediated transfection and transduction using retrovirus, lentivirus or other virus, e.g. vaccinia or, for insect cells, baculovirus. As an alternative, direct injection of the nucleic acid could be employed. In a preferred embodiment of the present invention, the STAT5 encoding nucleic acid is introduced into the cell in question using a retroviral vector.

Marker genes such as antibiotic resistance or sensitivity genes or genes encoding markers such as cell surface antigens or fluorescent proteins like green fluorescence protein may be used in identifying clones containing the introduced nucleic acid, as is well known in the art.

The cell of interest may be any cell that it is desirable to maintain. Reasons for maintaining a cell, in particular, a primary cell, in the form of a cell line is often because the particular cell type is useful for research including medical research purposes or it is a cell that can express a particularly desirable protein, e.g. an enzyme, antibody or hormone, that could be usefully produced in larger quantities than could realistically be extracted from isolated cells.

The description of the present invention concentrates on the generation of antibody producing human B-cells. However, it will be apparent to the skilled person that the invention could equally be applied to other cells of interest, e.g. T-cells, dendritic cells, APCs and natural killer (NK) cells. The ability to produce cell lines of antibody producing human B cells is very important as these cells may lead to the production of extremely valuable antibodies unavailable from other sources. For example, it is preferable that the cells in accordance with the first aspect of the invention are obtained from a patient who has shown signs of raising protective antibody against a pathogen or tumour cell. The production of a cell line using these cells will allow maintenance and direct or indirect extraction of the protective antibody in useful quantities, such that it can be tested and potentially produced into a pharmaceutical composition.

The genes encoding both the Ig heavy and light chains may be expressed in the cells and the antibody directly extracted or the genes may be retrieved from the cells and expressed in a second cell line, such as CHO, MKC etc., for production of the antibody protein. Preferably, the second cell line is a validated cell line in that it can be used to produce substances for use in humans. In other words, it is preferable that the second cell line is checked to ensure that it does not produce pathogenic agents e.g. viruses, prions etc.

In a preferred embodiment of the present invention, the method further comprises the step of halting the replication of the cells of the cell line thereby bringing about terminal differentiation of the cell so that the desired protein, expression product, e.g. can be produced and extracted either directly, or indirectly, e.g. by cloning the relevant gene into a second cell line and producing the protein from said second cell line. The protein may then be purified and used in the production of a pharmaceutical composition.

The present inventor has devised a mechanism by which the action of STAT5 on the cells can be switched off so as to induce terminal differentiation.

This step may conveniently be achieved by associating an inactivating agent with the STAT5 protein in the transformed cell. The inactivating agent may then be switched on or off depending on the stage of the cell in the development of the cell line.

Thus, in a second aspect of the present invention, there is provided a method of producing a cell line comprising cells of interest, e.g. antibody producing human B cells; said method comprising the steps of
  (a) obtaining said cells of interest;
  (b) incorporating into said cell a STAT5 protein in association with an inactivating agent;
  (c) allowing said cells to replicate by switching off said inactivating agent thereby rendering STAT5 active; and
  (d) maintaining said produced cell line.
The method may further comprise the step of
  (e) optionally cloning a cell from said cell line
  (f) inducing terminal differentiation of said cells by switching on said inactivating agent thereby rendering STAT5 inactive; and
  (g) extracting a desired protein expressed by the terminally differentiated cell.

A cell may be cloned from the cell line in order to produce a monoclonal antibody from B-cells. A cell need not be cloned if a combination of antibodies is needed.

The method may still further comprise the steps of
  (h) optionally extracting the Ig genes and expressing them in validated cell lines;
  (i) purifying said extracted protein; and
  (j) producing a pharmaceutical composition comprising said protein or nucleic acid encoding it.

The inactivating agent may be an inducible promoter/excision system such as cre-lox or FLP/FRT excision system.

Thus, the expression of STAT may be switched on or off using an inducible promoter, or its expression may be dependent on an inducible excision system, e.g. cre-lox or FLP/FRT. Further, antisense nucleic acid may be used, e.g. double stranded interfering RNA (RNAi) or DNA that produce RNAi may be used to control the expression of STAT.

In the above situation, step (f) of the method may be achieved by removing the inducer of the inducible promoter; activating the cre-lox or FLP/FRT excision system; or introducing antisense or RNAi.

In a preferred embodiment, the inactivating agent is a protein that is associated with said STAT5 protein as a fusion protein. Conveniently the gene encoding the inactivating agent may be fused to the STAT5 gene and expressed in the cell so as to produce the fusion protein. The inactivating agent may then be switched off by alteration to the fusion protein's environment. For example, the present inventor has successfully shown that the estrogen receptor and STAT5 can be produced in the desired cell as a fusion protein (STAT5-ER). The estrogen receptor acts as an inactivating agent to STAT5, as the fusion protein is inactive because it forms a complex with heat shock proteins in the cytosol preventing the STAT5 protein from reaching the nucleus. However, upon incubation with 4 Hydroxy-Tamoxifen (4HT), the fusion protein (STAT5-ER) dissociates from the heat shock proteins and is transported to the nucleus in its active form. Removal of 4HT results in cessation of the growth of the cells of interest as the expressed STAT5 and estrogen receptor remain associated with heat shock proteins as a complex and thus inactive. These cells then terminally differentiate. Thus, in this example, the inactivating agent ER can be switched on or off using 4HT.

Another example of an inactivating agent, which can be associated with the STAT5 protein is a transcription factor binding site upstream or downstream of the nucleic acid encoding the STAT5 protein, whereby expression of the STAT5 protein is under the control of the transcription factor. This inactivating agent can be switched on and off by the presence of absence respectively of a transcription factor (a transactivator). The presence or absence of the transactivator can be controlled by manipulating its expression or function in the cell.

This may conveniently be achieved by the provision in the cell of two plasmids, the first plasmid encoding the transcription factor (transactivator) and the second plasmid encoding STAT5. The second plasmid also comprising a nucleic acid binding site for the transactivator upstream of the nucleic acid encoding the STAT5 protein such that expression of the STAT5 is under the control of the transactivator. The inactivating agent may then be switched off by contacting the cell with an agent that inactivates the transactivator. By removing the agent the transactivator is active and allows expression of STAT5. An example of such a system is the tetracycline regulatable system such as described by Bujard and collaborators (Gossen, et al., 1995).

In a third aspect of the present invention, there is provided a nucleic acid construct for transforming cells so as to produce cell lines, said nucleic acid construct comprising nucleic acid sequence encoding a constitutively active STAT5 protein (STAT5a or STAT5b) and an inactivating agent such that expression of the nucleic acid produces a fusion protein comprising said STAT5 and the inactivating agent.

The nucleic acid construct may be DNA, cDNA, RNA or genomic DNA. Further it may be held within an expression vector, e.g. a plasmid or retroviral vector. Further, the nucleic acid construct may be operably linked to modulatory sequences such as promoters or transcription factor binding sites as mentioned above, which will aid its expression. The nucleic acid construct or vector comprising it may be contained within a host cell. In a preferred embodiment, the inactivating agent is the estrogen receptor.

In a fourth aspect, there is provided a kit for producing a cell line comprising cells of interest, said kit comprising at least a nucleic acid construct comprising nucleic acid encoding constitutively active STAT5 (STAT5a or STATb). The nucleic acid construct may also encode an inactivating agent in association with STAT5. The kit may further comprise a disassociation agent, e.g. 4HT, which is capable of disassociating STAT5 from the inactivating agent.

Recently, it was reported that ectopic expression of BCL-6 in human tonsil B cells results in an enhanced proliferation of the B cells and a considerable life span extension of these cells (Shvarts, 2002). The present inventor has extended these findings by showing that expression of BCL-6 in adult peripheral B cells also results in enhancement of the proliferative response. The BCL-6-transduced peripheral B cells expressed B cell activation markers and CD19 and CD20. In addition the inventor has observed a consistent cell surface expression of light chain Kappa (κ) and Lambda (Λ) indicating that BCL-6 inhibits differentiation of cell surface Ig+ B cells to plasma cells. Fearon and collaborators predicted that expression of BCL-6 allows self-renewal of germinal center and memory B cells (Reljic, 2000; Fearon, 2001). The inventor's findings that ectopic expression of BCL-6 into human B cells results in a dramatic extension of the proliferative response induced by CD40L and cytokines support this hypothesis.

Recent work has provided insight into the mechanism of control of B cell differentiation by BCL-6 since this protein appeared to repress Blimp-1 (Turner, 1994), which is driving plasma cell differentiation (Reljic, 2000; Shaffer, 2000; Shaffer, 2002). Repression of Blimp-1 by BCL-6 is indirect and mediated through the AP-1 complex (Vasanwala, 2002). Blimp-1 was shown to inhibit transcription of c-myc, which is essential for cell cycle progression of B cells cultured with CD40L and IL-4 (Lin, 1997). It is therefore likely that ectopic expression of BCL-6 in B cells turns off Blimp-1 and thereby enables continued expression of c-myc. It was previously demonstrated that cyclin D1 is selectively expressed in BCL-6-transduced cells, but its role in cell cycle progression in BCL-6 transduced B cells is not yet clear (Shvarts, 2002). Besides affecting cell cycle progression in B cells ectopic BCL-6 expression may also inhibit apoptosis. In this respect it is relevant to note that BCL-6 was shown to repress the programmed cell death (PDCD) gene 2, which appears to be associated with programmed cell death in thymocytes (Baron, 2002).

Given the important role of BCL-6 in B cell proliferation and differentiation it is of interest to know how this gene is regulated. The presence of STAT5 consensus sites in the BCL-6 promoter (Ohashi, 1995) prompted the inventor to examine whether STAT5 regulates BCL-6. He employed a CA-STAT5b-ER construct to demonstrate that BCL-6 is upregulated by STAT5b. Importantly, the upregulation of BCL-6 transcripts was insensitive for the protein synthesis inhibitor cycloheximide, indicating that BCL-6 is a direct target of STAT5b, at least in B cells.

Further support for regulation of BCL-6 expression in B cells by STAT5b was provided by the inventor's observation that constitutive expression of a CA-STAT5b mutant results in extension of B cell proliferation similar as BCL-6. Promotion of B cell expansion by ectopic STAT5b expression is not due to EBV transformation, since the STAT5-transduced B cells are LMP-1 and EBNA 1/2 negative and also lacked CD20, which is expressed on all EBV-transformed B cells. Moreover, B cells transduced with a regulatable CA-STAT5b construct only expand with STAT5b in the on mode, which excludes that the enhanced proliferative capacity of the transduced B cells is caused by a secondary transforming event. The observations that STAT5b directly regulates BCL-6 suggest that inhibition of terminal differentiation is one manner by which the proliferative response towards CD40L and IL-2 or IL-4 is dramatically extended by ectopic expression of CA-STAT5b. The cells that express CA-STAT5b-ER and grow with 4HT still need CD40L and either IL-2 or IL-4 for optimal growth. Thus, activation of STAT5 in this system is by itself not sufficient to fully replace the signal provided by the growth factors. Obviously other signal transduction pathways, triggered by the cytokines and CD40 ligation, like the PI-3K, NF-kB and p38 kinase (Andjelic, 2000; Dadgostar, 2002), are needed to induce cell cycle progression. Although STAT5b-ER B cells cultured with 4HT but without CD40L and cytokines do not expand, they do have a survival advantage compared to cells cultured without 4HT (results not shown). Thus it appears that over expression of CA-STAT5b in addition to inhibiting terminal differentiation has a major effect on survival of the mature B cells, which may be independent of BCL-6. Support for the notion that STAT5b may directly regulate factors involved in B cell survival comes from a study that found evidence for the involvement of STAT5 in expression of Bcl-2 and Bcl-$X_L$ in T cells (Lord, 2000). Bcl-$X_L$ is also induced by expression of a constitutive active mutant of STAT5 in the cell line BAF3 (Nosaka, 1999). In addition of STAT5 consensus binding sites in the promoters of Bcl-2 and Bcl-$X_L$. Thus it is likely that STAT5 forms participate in regulation of anti apoptotic genes in primary B cells as well.

An important question raised by the inventor's findings is whether BCL-6 expression is strictly dependent on STAT5. The data from the literature do not provide evidence in favour of the hypothesis that STAT5a and b are required for BCL-6 expression or function but do also not refute this idea. BCL-6 deficient mice lack germinal centers (Dent, 1997; Ye, 1997; Fukuda, 1997). The B cells of these mice are able to produce IgM and IgG1, indicating that there is capacity for isotype switching (Toyama, 2002). The Ig produced in BCL-6-deficient mice lack somatic mutations (Toyama, 2002). STAT5a and b double deficient mice have drastically reduced numbers of B cells in the periphery (Sexl, 2000). However, the absolute numbers of B cells in the spleen were reported to be similar as in wild type mice. These mice were also shown to produce IgM and IgG1 (Sexl, 2000) but it is unknown whether germinal centers are formed in STAT5a and b double deficient mice and it is also unknown whether somatic mutations occur in the Ig genes of these mice. Obviously analysis of BCL-6 expression in STAT5a/b double deficient mice will answer the question whether STAT5 proteins are required for BCL-6 expression.

Although upregulation of BCL-6 may play a role in the control of B cell survival and growth by STAT5, a number of differences between CA-STAT5b transduced cells and BCL-6-transduced B cells suggest that regulation of BCL-6 is not the only explanation for the effects of continued activation of STAT5b on cultured human B cells. A first difference is that transduced B cells with STAT5b in the on mode grow faster than BCL-6-transduced B cells. Another notable difference is that BCL-6-transduced B cells consistently express cell surface Ig on the cell surface, while CA-STAT5b-transduced cells gradually lose sIg expression upon continued in vitro culture (results not shown). This loss of sIg expression is not accompanied by an increase in Ig secretion, an increase in CD38 expression or induction of CD138 and is therefore not a consequence of differentiation into plasma cells. Moreover, although the cell surface expression of a number of B cell activation antigens like CD40, CD70, CD80 and CD86 is very similar, CA-STAT5b-transduced cells express much higher levels of CD25 than BCL-6-transduced cells. Obviously these differences should be caused by additional transcriptional programs that are turned on the high level of STAT5b expression combined with a continued activation of STAT5b. Further analysis of the genes that are turned on by addition of 4HT to CA-STAT5b-ER transduced B cells will provide further information about the role of STAT5b in survival, growth and differentiation of B cells.

Accordingly, in a fifth aspect of the present invention, there is provided a method for screening for substances capable of mimicking the activity of CA-STAT5 comprising
1) contacting a test substance with a cell capable of expressing BCL-6 in a first reaction medium;
2) contacting CA-STAT5 with a cell capable of expressing BCL-6 in a second equivalent reaction medium; and
3) comparing the expression of BCL-6 in the first reaction medium with that of the second reaction medium to determine if the test substance is capable of mimicking the activity of CA-STAT5.

Preferably, the activity of CA-STAT5 is its ability to regulate the expression of BCL-6 in mammalian cells, preferably B-cells.

The cell may inherently/naturally express BCL-6, or the cell may have been engineered to express BCL-6. The test substance and/or STAT5 (STAT5a or STAT5b) may be expressed within the cell. In other words, the cell may have been engineered to express the test substance and/or STAT5.

The expression of BCL-6 of the first and second reactions may be compared by determining whether the cell cease growing and eventually terminally differentiate.

An alternative method for screening for substances capable of mimicking STAT5 (preferable STAT5b) comprises the steps of
1) transducing a cell, e.g. a B cell, with STAT5-ER;
2) culturing the cell in the presence of 4HT;
3) introducing a cDNA library into the cell via a viral vector, e.g. a retroviral vector;
4) turning off STAT5 by removing 4HT; and
5) selecting those cells which continue to replicate.

Those cells which continue to replicate will comprises a gene encoding a protein capable of mimicking the activity of STAT5. Therefore, the method may further comprise the step of sequencing nucleic acid from those cells which continue to replicate.

Aspects and embodiments of the present invention will now be illustrated, by way of example, with reference to the accompanying figures. Further aspects and embodiments will be apparent to those skilled in the art. All documents mentioned in this text are incorporated herein by reference.

B Cell Isolation

Tonsil were obtained from tonsillectomy from the department of surgery for children of the Free University of Amsterdam. T cells were depleted using anti-CD4 and anti-CD8 microbeads (Miltenyi Biotec). Next cells were incubated with anti-CD19 FITC conjugated (Dako) and anti-CD3 phycoerythrin (PE) conjugated (Becton Dickinson), followed by sorting of the CD19+ CD3⁻ population. The resulting B cells were 95 to 98% pure upon reanalysis.

Retroviral Constructs and Production of Recombinant Retrovirus

Constitutive active mutants of STAT5a and b have been described previously (Ariyoshi et al., 2000; Onishi et al., 1998). DNAs encoding these mutants were obtained from T. Kitamura, (IMSUT, Tokyo, Japan). These DNA's were ligated into LZRS-linker-IRES-GFP vector that was described previously (Heemskerk et al., 1997; Heemskerk et al., 1999). The retroviral plasmids were transfected into a helper-virus free amphotropic producer cell line Phoenix-A, a derivative of the human embryonic kidney cell line 293 (Kinsella and Nolan, 1996) (a kind gift of Dr. G. Nolan, Stanford University, Palo Alto, Calif.), using Fugene-6 (Roche Diagnostics) according to manufacturers protocols. Two days later selection of transfected cells started by the addition of 2 μg/ml puromycin (Clontech Laboratories). Ten to 14 days after transfection $6 \times 10^6$ cells were plated per 10 cm petridish (Becton Dickinson, San Jose, Calif., USA) in 10 ml complete medium without puromycin. The next day the medium was refreshed and on the following day retroviral supernatant was harvested, centrifuged and frozen in cell free aliquots at −70° C. This approach affords a reproducible rapid, large scale and high titer retroviral production of over $3 \times 10^6$ infectious virus particles/ml.

A CA-STAT5b estrogen receptor (ER) fusion construct was made as follows: A PCR was performed with the N604H STAT5b mutant (Ariyoshi et al., 2000; Onishi et al., 1998) to introduce a BglII site in lieu of the stop codon. A XhoI/BglII digestion product was generated that contained the mutation. This was ligated with a BamHI/EcoRI digest of pBS-ER (C term) and a XhoI/EcoR1 digest of pBS-SK+ to create ΔCA-STAT5bER. A XhoI/NotI digest of LZRS CASTAT5b-IRES-ΔNGFR was then ligated to a partial NotI/XhoI digest of pBS ΔCA-STAT5bER to create LZRS CA-STAT5bER. Using this we made a construct with CA-STAT5b-ER downstream of IRES and a Nerve Growth Factor Receptor (ΔNGFR) a deleted, signalling-incompetent mutant of the NGFR, kindly provided by Dr C. Bonini (Bonini, 1997).

Retroviral Transduction Method

The recombinant human fibronectin fragments CH-296 transduction procedure (RetroNectin™; Takara, Otsu, Japan) was based on a method developed by Hanenberg et al (Hanenberg et al., 1997; Hanenberg et al., 1996). Non-tissue culture-treated 24 wells plate (Costar) were coated with 0.5 ml of 1 μg/ml recombinant human fibronectin fragment CH-296 at room temperature for 2 hours or overnight at 4° C. The CH-296 solution was removed, followed by incubation with 2% human serum albumin (HAS) in phoshate buffered saline (PBS) for 30 min at room temperature, followed by washing once with PBS. $5.10^5$ B cells were plated in 0.25 ml Iscove's medium (Life Technologies) plus 10% fetal bovine serum (FCS) mixed with 0.25 ml of thawed retroviral supernatant, incubated 6 hours at 37° C. Next 0.25 ml of supernatant was removed and 0.25 ml of fresh retroviral supernatant was added and incubated at 37° C. overnight. The next morning cells were washed and transferred to 24 wells tissue culture treated plate (Costar, Badhoevedorp, Netherlands) with irradiated CD40L expressing L cells, IL-2 (20 U/ml) and IL-4 (50 ng/ml).

Cell Culture

B cells were cultured in Iscove medium (Life Technologies) together with 10% FCS at 37° C. in humidified air containing 5% $CO_2$. CD40L expressing L cells, 80 Gray irradiated, were seeded $5.10^4$ cells per well in 24 wells tissue culture treated plate (Costar). $50.10^4$ sorted B cells were added together with IL-2 (20 U/ml) and IL-4 (50 ng/ml). After one week the cells were used for retroviral transduction. After transduction B cells were cultured again with irradiated CD40L expressing L cells, IL-2 and IL-4. After one week the cells were cultured with irradiated CD40L expressing L cells, IL-2 and IL-10 for one week then followed by IL-2 and IL-10 followed by IL-6 (30 U/ml).

Phenotyping

Antibodies against the human molecules CD3, CD19, CD20, CD38, CD40, CD80, CD45, HLA-DR, CD27, CD56, CD70, (Becton Dickinson) directly labeled with PE, PerCp or APC and IgM, kappa light chain, Lambda light chain, CD138, directly labeled with PE (Dako) were used for flow cytometry analysis. Stained cells were analyzed using a Facscalibur (Becton Dickinson) and FACS data was processed with Cell Quest computer software (Becton Dickinson).

Elisa

IgM, IgG and subtypes and IgA in culture supernatants were detected by ELISA using rabbit anti-human isotype specific antibodies (Dako) as capture antibodies and Alkaline Phosphatase-conjugated IgM, IgG and IgA (Dako), followed by Alkaline Phosphatase substrate (Sigma). Human serum protein calibrator (Dako) were used for the standard curve.

RT-PCR

RNA was harvested from thawed pellets with RNeasy® mini kit (Qiagen). RNA was reverse transcribed in volume of 20 μL, containing 5× first strand buffer, 500 μmol/L dNTP's, 25 μg/L Oligo (dT), 200 U superscript II RT (Life technologies). One microliter of cDNA was subjected to PCR in a 50 μl solution containing 20 mmol/L Tris-HCL, 50 mmol/L KCL, 1.5 mmol/L $MgCl_2$, 5 mmol/L dNTP's, 2.5 U Taq DNA polymerase (Life Technologies), and 30 pmol of each primer. The HPRT PCR were as follows: 7 min denaturing step at 94° C. followed by 30 cycles of 30 sec at 94° C., 30 sec at 65° C., and 30 sec at 72° C., and a final 7 min extension at 72° C. The LMP-1 and EBNA PCR were as follows: 7 min denaturing step at 94° C. followed by 30 cycles of 30 sec at 94° C., 30 sec at 52° C., and 30 sec at 72° C., and a final 7 min extension at 72° C. The oligonucleotides used for reverse transcriptase (RT) PCR were:

| | |
|---|---|
| HPRT forward, | 5'TATGGACAGGACTGAACGTCTTGC3', |
| HPRT reverse, | 5'GACACAAACATGATTCAAATCCCTGA3', |
| LMP-1 forward, | 5'GCGACTCTGCTGGAAATGAT3'; |
| LMP-1 reverse, | 5'GACATGGTAATGCCTAGAAG3'; |
| EBNA1/2 forward, | 5'AGCAAGAAGAGGAGGTGGTAAG3'; |

-continued

| | |
|---|---|
| EBNA1/2 reverse, | 5'GGCTCAAAGTGGTCTCTAATGC3'. |
| BCL-6 forward, | 5'AAGGGTCTGGTTAGTCCACAG3' |
| BCL-6 reverse, | 5'GGTCACACTTGTAGGGTTTGTC3' |
| c-Myc forward | 5'TCGGATTCTCTGCTCTCCTC3' |
| c-Myc reverse | 5'TTCCGCAACAAGTCCTCTTC3' |
| hTERT forward | 5'CTGCAGGCGTACAGGTTTCACG3' |
| hTERT reverse | 5'CCTCAGACTCCCAGCGGTGC3' |

Results

Effect of Constitutive Active Mutants of STAT5 on Growth of Human B Cells

It has been reported that mice deficient for STAT 5 a and b have defects in their B cells (Sexl et al., 2000). The number of mature B cells in peripheral blood is strongly reduced in these mice but not in the spleen or bone marrow. In addition there are deficiencies in the early B cell compartment as indicated by reduced numbers of pro- and pre B cells in the STAT 5a and b double knock out mice (Sexl et al., 2000). The finding that introduction of cDNA encoding an active STAT5 mutant induces IL-3-independent growth of the pro B cell line BAF3 (Ariyoshi et al., 2000; Onishi et al., 1998) suggested that activation of STAT 5 a and b is required for cell cycle progression in early stages of the B cell lineage. However, whether activation of STAT5 is necessary for proliferation of mature B cells is unknown. The inventor has examined this by analyzing the effects of active mutants of STAT5a and b on in vitro expansion of mature B cells.

Figure 1:
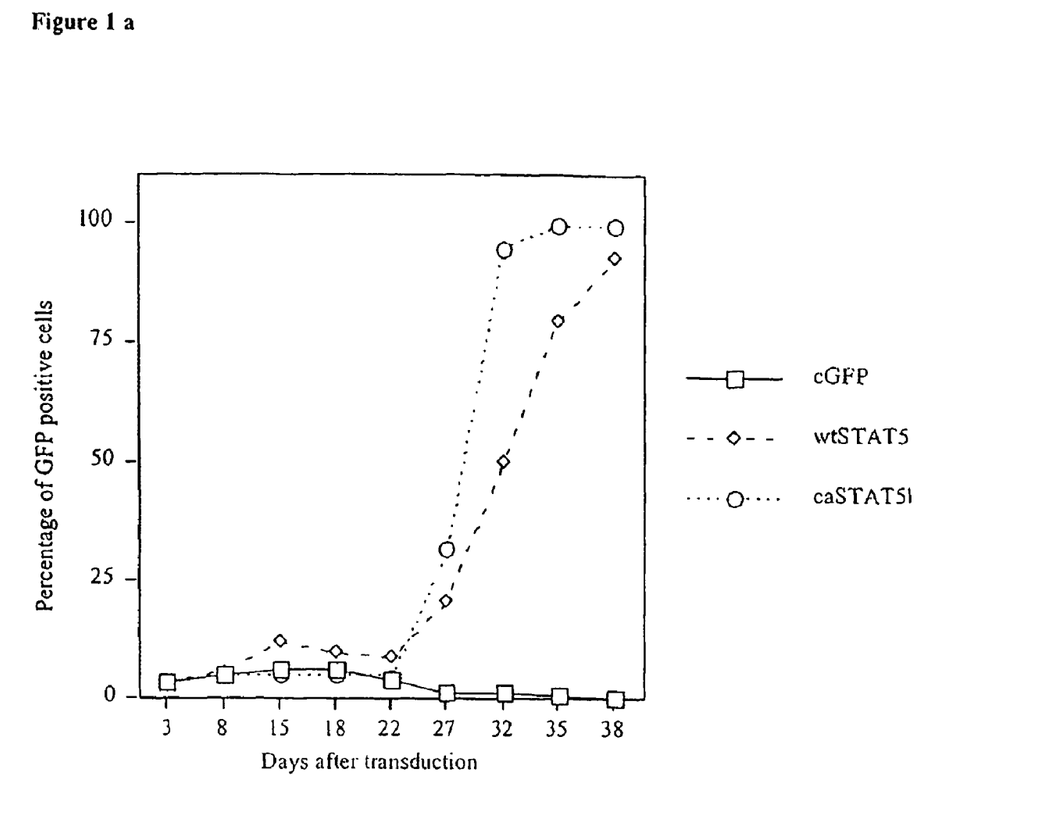
FIG. 1 Expression of CA-STAT5b leads to survival and expansion of B cells, while expression of wt STAT5b results in survival only. B cell were isolated from a suspension of tonsil, cultured with CD40L IL2 and Il-4 and transduced with control (c) GFP, wild type (wt) STAT5b-GFP or constitutive active (ca) STAT5b-GFP and cultured further with CD40L, IL-2 and IL-4 (a) Percentages of GFP+ cells (b) counted numbers of cells in the cultures FIG. 2 CA-STAT5b transduced growing B cells fail to express EBV associated antigens LMP1 and EBNA 1 or 2
Figure 1B:
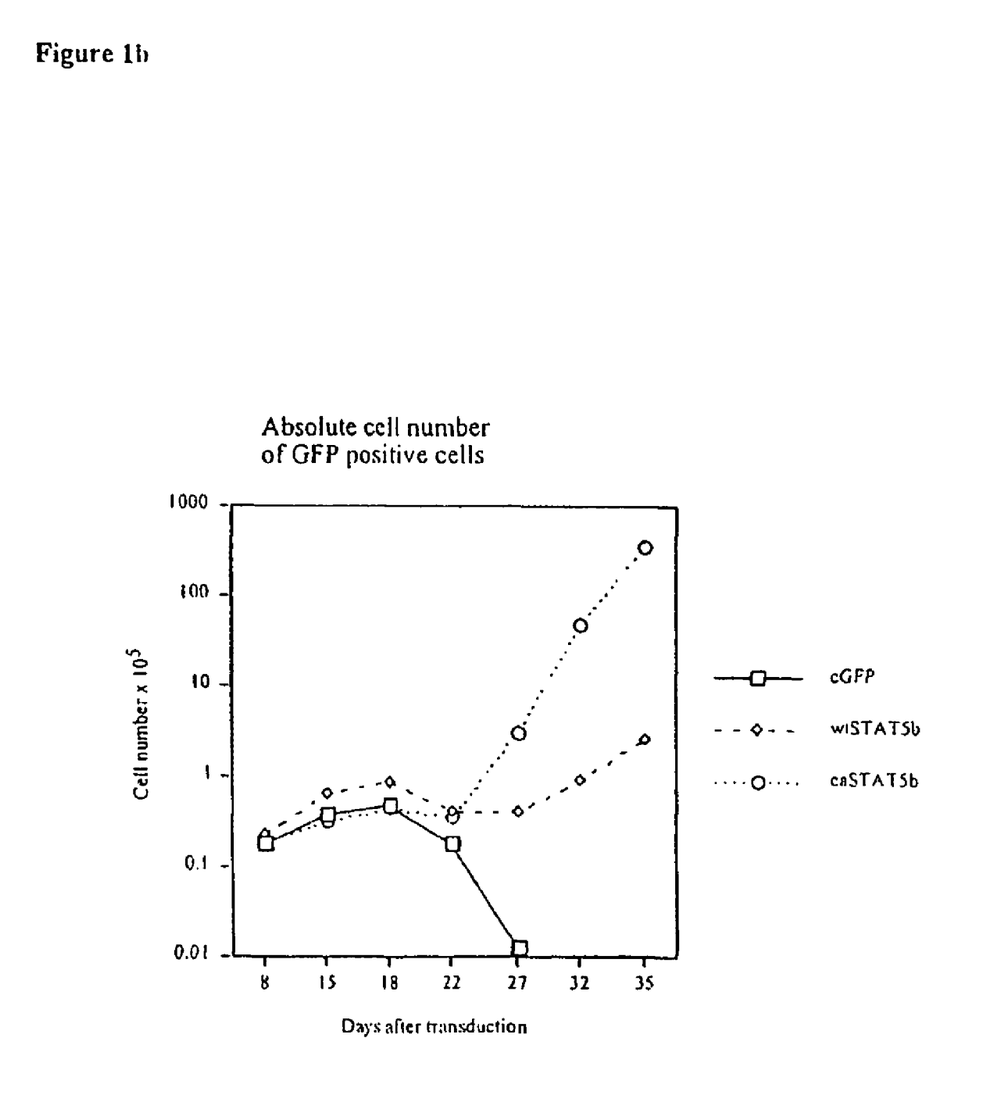

Tonsillar CD19+ B cells were isolated as indicated in materials and methods. These cells were cocultured with IL-2, IL-4 and mouse fibroblasts that were transfected with CD40L (CD154). Two days later the cells were transduced with constitutive active (CA) STAT5-IRES-GFP (STAT5a and STAT5b), with wild type STAT5b or with a control IRES-GFP. Transduction efficiencies were 5% (FIG. 1). The cells were expanded the first week in CD40L and IL-2 and IL-4 and then in a combination of CD40L, IL-2 and IL-10 to promote further growth. The first three weeks of culture that percentages of GFP+ cells in the various cultures didn't change. However, starting with 3 weeks of culture, the percentage of GFP+ cells in the cultures transduced with CA-STAT5a (not shown) and b (FIG. 1) increased over time. At week 7 the control-transduced and the untransduced B cells started to die. At week 8 >95% of the CA-STAT5a and b-transduced cultures were GFP+ and continued to expand. B cells transduced with wild type STAT5b survived but did not expand (FIG. 1a and b), indicating that activation of STAT5 is required for expansion of the B cells.

To test the cytokine requirements of the CA-STAT5-transduced B cells, the culture expanded in IL-10 were split and cultured further with IL-10, IL-6 or no cytokines. The cells of all three cultures expanded equally well. The finding that the CA-STAT5-transduced B cells expand in the absence of cytokines may suggest that either CA-STAT5 bypasses a cytokine mediated signal leading to continuous cell cycle progression or the active STAT5 induces secretion of a cytokine that mediates cell growth. A second experiment with tonsillar B cells of another donor gave identical results. In that experiment, the transduction efficiencies at the initiation of the culture were between 10 and 20%. Similarly as in the first experiments the untransduced and the control-transduced cells ceased growing after 6-7 weeks while the CA-STAT5a and b transduced cells continued to expand.

The inventor's findings suggest that CA-STAT5-transduced cells had an extended replicative life span as compared to normal B cells. Since Epstein Barr Virus (EBV) can immortalize B cells and EBV transformed cells can "spontaneously" appear in cultures of tonsillar B cells, it was important to exclude that life-span extension of the CA-STAT5-transduced cells was not due to EBV transformation. EBV-transformed B cells invariably express CD20 and the finding that the STAT5-transduced B cells lack CD20 suggested already that they are not EBV transformed. This was confirmed by the observation that the CA-STAT5b-transduced B cells did not express LMP-1 or EBNA1/2 mRNA as assessed by a sensitive RT-PCR (FIG. 2).

Figure 2:
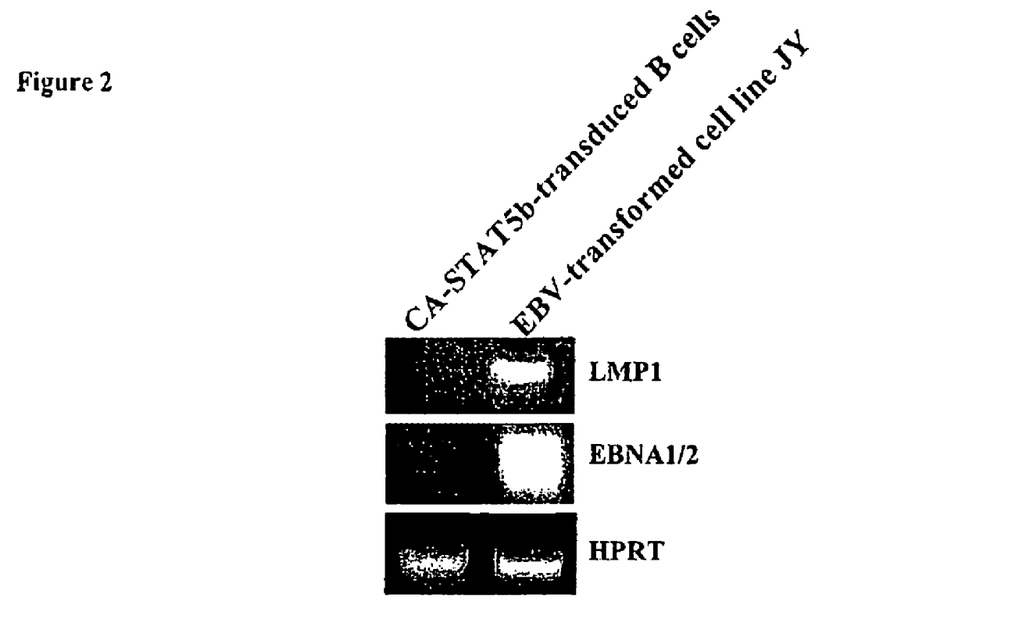

The experiments depicted in FIG. 1 and 2 were performed with tonsillar B cells. To assure the general validity of this approach to extend the life span of the B cells, the inventor cultured peripheral blood B cells with CD40L, IL-2 and IL-4 and transduced these cells with CA-STAT5b. Around day 30 after initiation of the culture the proportion of GFP+ cells began to increase to reach 100% two weeks later (results not shown) similar to what the inventor observed with tonsil B cells.

Phenotype of the Expanded B Cells

After three weeks of culture that cells expressed low levels of CD19 and CD20. In addition 83% of the cells at that time point expressed CD38 (results not shown). These results indicated that many B cells were differentiated into plasma cells. The phenotype of the "selected" CA-STAT5-transduced cells (>95% GFP+) is different. The level of CD19 is higher but lower than on freshly isolated B cells (Table 1). Expression of CD38 on CA-STAT5-transduced cells dropped in time and its expression eventually became lower than on the cells cultured for 3 weeks. The CA-STAT5-transduced cells remained CD20 negative, but were also CD27 negative. This phenotype strongly suggests that the cells are not plasma cells since plasma cells express only very low levels of CD19, are CD38+ and CD27 positive. The CA-STAT5-transduced cells furthermore were negative for cell surface IgM (results not shown).

Cloning of STAT5-Transduced B Cells.

Figure 3:
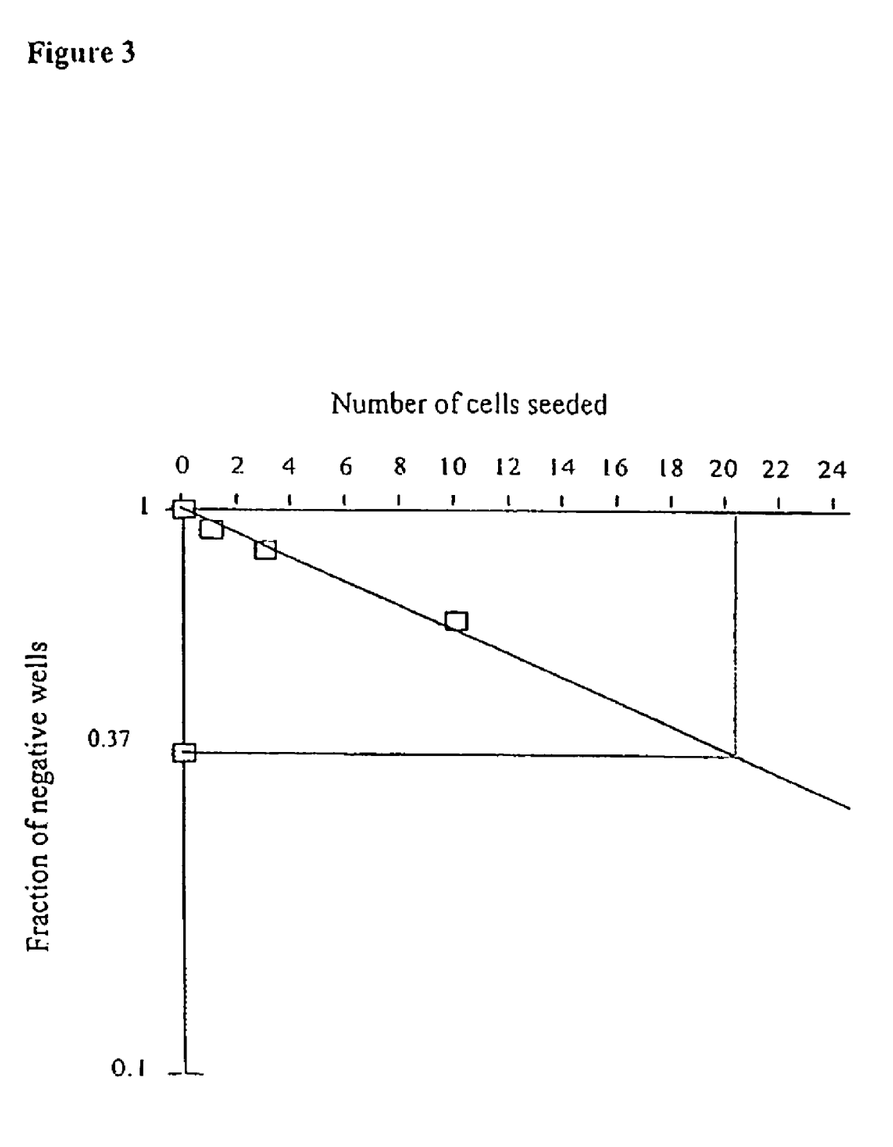
FIG. 3 Cloning efficiency of CA-STAT5b-transduced B cells. Following 2 months of culture the CA-STAT5b-GFP+ cells were cloned by sorting of 1, 3, 10 and 100 cells per well of a round bottomed microtiter plate. Cultures were counted 3-4 weeks later.

Given the spectacular extension of the replicative life span of the CA-STAT5-transduced B cells, it was of interest to investigate whether these cells can be cloned. Immortalization of B cells does not necessarily lead to high cloning efficiencies since it is difficult to clone EBV-transformed B cells. The CA-STAT5-transduced B cells were seeded at limiting dilutions in well of a 96 round-bottomed well tissue culture plate. 288 wells were seeded with 1 cell/well, 192 with 3 cells/well and 96 with 10 cells/well. On the basis of the possibility that the STAT5-transduced B cells produce an autocrine growth factor, the inventor used irradiated (40 Gy's) STAT5-transduced B cells as feeder cells. Growing cultures were visible 14-21 days after the outset of the micro cultures. The appearance of these clones was not due to outgrowth of the irradiated B cells since the plates seeded with irradiated cells only did not yield any growing cultures. The cloning efficiency as calculated from the results of counting the wells with growing cultures was 7% (FIG. 3). Fifty clones were transferred to wells of a 24 well plate to test the stability of the clones. All clones could be expanded for at least 4 weeks. These results indicate that the STAT5-transduced B cells can be cloned with remarkable high efficiency.

Ig Production by Poly- and Monoclonal CA-STAT5-Transduced B Cells.

The IgG production of the CA-STAT5-transduced B cells was tested using an ELISA as described in material and methods. Half a million cells were cultured for 3 days in medium with 5% FCS after which the supernatant was harvested and tested. The parental CA-STAT5-transduced cells produced IgG, but the amount of IgG decreased upon continuation of the culture. While in some experiments exemplified in Table 2, first column, around 1 μg IgG/ml were produced, the levels were much less when the culture was tested at a later time point of culture (exemplified in exp. 2). Some clones produced IgG in the same order of magnitude (Table 2), while other clones failed to produce detectable IgG (data not shown). These data seem to indicate that CA-STAT5b-transduced B cells lose their capacity to produce Ig upon prolonged culture.

Generation of B Cell Lines Following Induction of CA-STAT5b Expression with Tamoxifen.

Figure 4:
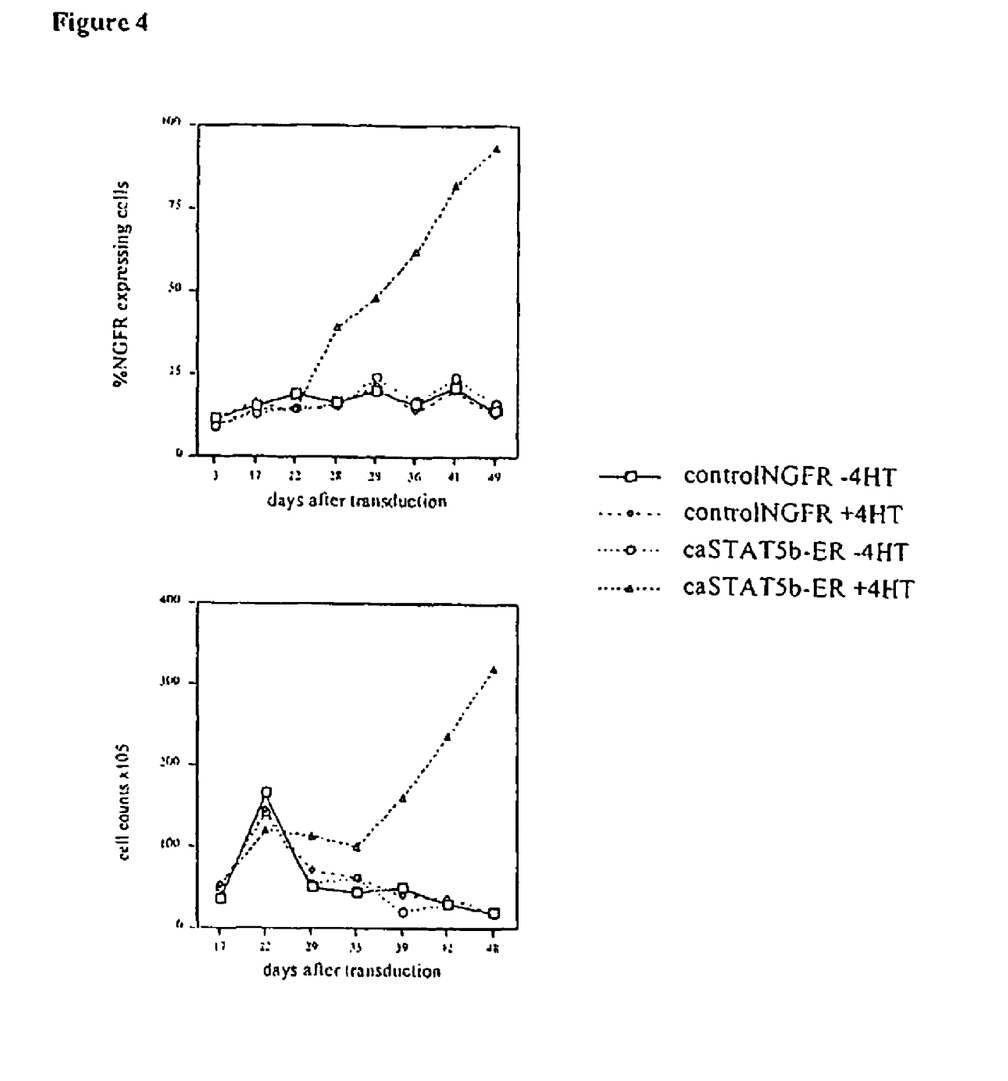
FIG. 4 Tosillar B cells were cultured in CD40L, IL-2 and IL-4 and transduced with the CA-STAT5bER-IRES-ΔNGFR or with control-IRES-ΔNGFR. Both cultures were split, one part was cultured without and one with 1 μM 4 Hydroxy-Tamoxifen (4HT).
Figure 5:
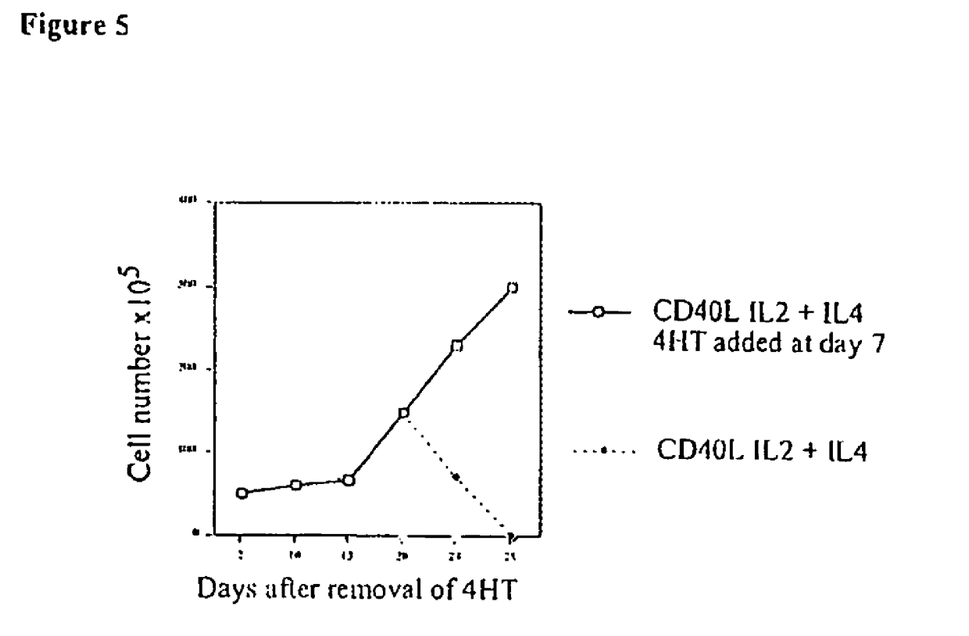
FIG. 5 Growth of B cells is dependent on continued functional expression of CA-STAT5b. B cells transduced with CA-STAT5bER-IRES-ΔNGFR were cultured with 4HT till 100% of the cells expressed the transduced ΔNGFR. The cells were then cultured without the hormone for 7 days after which the culture was split. One part was cultured further with 4HT and the other without 4HT.

The observation that long term cultured lines of CA-STAT5b-transduced B cells often lose their capacity to produce Ig raise the question whether or not these cells have irreversibly lost their capacity to differentiate into Ig-producing cells. If CA-STAT5b reversibly inhibits terminal differentiation it might be possible to induce terminal differentiation by turning off CA-STAT5b. To examine this the inventor prepared a fusion of the estrogen receptor (ER) with CA-STAT5b. The fusion product is expressed in the transduced cells as an inactive complex with heat shock proteins. Upon incubation with 4 Hydroxy-Tamoxifen (4HT) the fusion product dissociates and is transported to the nucleus. Tonsillar B cells were transduced with CA-STAT5bER-IRES-ΔNGFR and cultured in CD40L, IL-2 and IL-4 in the presence or absence of 1 μM 4HT. FIG. 4 clearly shows that growth selection of CA-STAT5b expressing cells (ΔNGFR+) only occurred in the presence of 4HT. Importantly, removal of 4HT resulted in cessation of the growth of the B cells and eventual death. B cells transduced with CA-STAT5bER cultured with CD40L, IL2 and IL-4 cultured in the absence 4HT initially proliferated, but they ceased to grow after 14-20 days. Three days later the cells started to die. When 4HT was added back after 7 days, the cells survived and continued to grow later (FIG. 5). These results indicate that CA-STAT5b-induced growth of the B cells is not a consequence of irreversible genetic changes induced by CA-STAT5b transforming the B cells but is only dependent on continued functional expression of CA-STAT5b.

The CA-STAT5b-ER transduced B cells cultured in CD40L, IL-2, IL-4 and 4HT express low levels of cell surface IgM with 45% kappa and 40% lambda chain expression indicating that they are polyclonal (FIG. 6). The cells were negative for cell surface IgD and a small percentage (1-2%) expressed IgG an lacked IgM. Furthermore they express CD38, CD40, CD70, CD80 and HLA-DR but are weakly positive for CD20 and negative for CD27. CD25 was highly expressed on these cells (FIG. 8) consistent with the fact that STAT5b directly controls CD25 (IL-2Rα) transcription [John, 1996 John, S., Robbins, C. M., and Leonard, W. J. (1996). An IL-2 response element in the human IL-2 receptor alpha chain promoter is a composite element that binds Stat5, Elf-1, HMG-I(Y) and a GATA family protein. Embo J 15, 5627-5635.

John, S., Vinkemeier, U., Soldaini, E., Darnell, J. E., and Leonard, W. J. (1999). The significance of tetramerization in promoter recruitment by Stat5. Mol Cell Biol 19, 1910-1918; John, 1999].

The finding that cultures of tonsil B cells transduced with CA-STAT5b-ER contained IgM+ B cells and only a few IgG+ B cells might be a consequence of the fact that tonsil B cells are mainly IgM+ cells. However it was also possible that expression of CA-STAT5b leads to selective outgrowth of IgM+ B cells. Therefore the inventor examined the effects of this mutant on growth of IgG+ cells. For these experiments he used peripheral blood (PB) B cells of adults. The inventor cultured purified PB B cells, transduced them with CASTAT5b-ER-IRES-GFP. The transduced B cells were then separated in IgM+ and IgG+ cells and cultured further in the presence of 4HT for 35 days. FIG. 7 clearly shows that expression of CASTAT5b-ER-IRES-GFP results in 4HT dependent growth of both IgM and IgG positive B cells. Further analysis of the phenotypes of these cells revealed that the phenotype of the IgG+ cells with respect to expression of CD25, CD38, CD40, CD70, CD80, HLA-DR, CD20 and CD27 was the same as the phenotype of the cultured tonsil B cells (results not shown).

Antibody Production of B Cells Transduced with CA-STAT5bER

A tonsillar B cell culture was established by culturing CA-STAT5bER-transduced B cells with CD40L, IL-2, IL-4 and 4HT. After selection of the ΔNGFR+ cells expressing (CA-STAT5bER) a line was established that was 4HT dependent (see previous paragraph). The inventor observed that this line failed to secrete IgG but made some IgM. Also when the cells were transferred in IL-2 and IL-10 and cultured for 3 days these cells did not make any Ig. However when they were first cultured in CD40L, IL-2 and IL-4 for 14 days without 4HT, the cells became permissive for IL-2/IL10 induced differentiation to Ig-producing cells (700 ng IgM ml/$10^6$ cells)

The inventor has described as an example of the present invention, a method to expand and to clone human B cells. Introduction of a constitutive mutant of STAT5a or b confers a dramatic replicative lifespan extension to the human B cells. Interestingly, the CA-STAT5-transduced B cells eventually grow in a cytokine independent manner. This is not due to EBV transformation since the STAT5-transduced B cells are LMP-1 and EBNA 1/2 negative. In addition the STAT5-transduced B cells lack CD20, which is expressed on all EBV-transformed B cells.

The mechanism underlying the cytokine independency of the CA-STAT5-transduced B cells is yet unknown. One possible explanation for the cytokine independence is that expression of CA-STAT5 results in a production of an autocrine growth factor. This is not a remote possibility since there is a cytokine, the IL-6-like cytokine Oncostatin M (OSM) that is a direct target of STAT5. One other possibility is that CA-STAT5 by itself induces continued cell cycle progression. CA-STAT5 may also prevent terminal differentiation of the B cells to plasma cells, which is accompanied with increasing cell death. This notion is consistent with the observation that B cells transduced with CA-STAT5bER, which grew in the presence of 4HT, became permissive for differentiation only after removal of 4HT.

The phenotype of the CA-STAT5-transduced B cells is reminiscent of activated CD19+CD20− (memory) B cells. It needs, however, to be noted that the cells are negative for CD27, which is normally expressed on memory B cells. Since the cells still express CD19 and CD40, which are absent on plasma cells, they have not been differentiated to the plasma cell stage. This could also be an explanation for the low and variable production of Ig by B cells that constitutively express functional CA-STAT5b. To overcome this problem, the inventor has successfully expressed an inducible CA-STAT5b, which allowed them to expand the B cells with CA-STAT5b in the on mode and to induce terminal differentiation of the B cells after turning off STAT5b. The observation that 4HT induces growth of B cells expressing a CA-STAT5bER fusion protein not only demonstrates that growth of the B cells is dependent only on functional, nuclear, expression of the STAT5b mutant but also presented a manner to induce terminal differentiation to plasma cells by removal of 4HT. Indeed, one B cell culture that failed to secrete IgG or IgM when cultured in 4HT became permissive for terminal differentiation 14 days after removal of 4HT. This observation strongly suggests that CA-STAT5b while promoting survival and growth of the B cells inhibits terminal differentiation.

Thus, as an example of the present invention, a method is provided with which one can expand and clone B cells in which terminal differentiation is inhibited. Once clones have been established by turning off CA-STAT5 one should be able to induce Ig production to screen for clones producing antibodies with a desired specificity. The Ig genes from selected CA-STAT5ER-transduced B cells can be retrieved and expressed under control of strong promoters in established cell lines such as CHO or myeloma cell lines (Little et al., 2000). Modified CHO cells have already been used to express murine Ig genes and Ig transfected CHO cells produce high levels of monoclonal antibody (10-20 µg/ml).

Ectopic Expression of BCL-6 into Human Peripheral Blood B Cells Results in Extension of the Replicative Life Span of the Cells and Maintenance of Cell Surface Immunoglobulin Recently it was reported that ectopic expression of BCL-6 in human tonsilar B cells of young children results in a growth advantage of B cells when cultured in CD40L, IL-2 and IL-4. These cells expressed CD19 and were negative for CD3 and CD56. To study whether BCL-6 also affects the proliferative capacity of adult peripheral blood B cells, the inventor introduced BCL-6-IRES-GFP into human B cells cultured with CD40L expressing L cells, IL-2 and IL-4. Expression of BCL-6 results in a growth advantage of the peripheral B cells expressing the marker GFP from 10 days after transduction of BCL-6. To obtain information about the phenotype of these cells, the inventor performed an extensive analysis with a panel of monoclonal antibodies. BCL-6 transduced B cells expressed CD19 but are negative for the T and NK cells markers CD3 and CD56. In addition the BCL-6-transduced cells expressed CD20, were very weakly positive for CD38 but were negative for the memory B cell marker CD27 and the plasma cell marker CD138. Furthermore the cells expressed the activation markers HLA-DR, CD40 and CD70 and were weakly positive for CD80 and CD25. Importantly, the BCL-6-transduced B cells expressed cell surface Ig κ (Kappa) or λ (Lambda) consistent with the fact that these cells are arrested in the differentiation into cell surface Ig negative plasma cells.

These data confirm the earlier data with tonsillar B cells, indicating that when B cells are blocked in their differentiation, they grow much longer in response to CD40L and cytokines.

BCL-6 is Regulated by CA-STAT5b

Factors that promote growth of B cells activate STAT5, which may potentially control BCL-6 expression since inspection of a 1.5 KB promotor of BCL-6 (Ohashi, 1995) revealed the presence of two STAT5 consensus sites raising the possibility that STAT5 regulates BCL-6. To examine this the inventor employed the recombinant viral construct harboring CA-STAT5b-ER upstream of IRES-(Δ) delta NGFR. ΔNGFR is a truncated, signaling incompetent mutant of the nerve growth factor receptor (Bonini, 1997). Following transduction the ΔNGFR is expressed on cell surface and can be detected with a monoclonal antibody (Bonini, 1997). Upon transduction the CASTAT5b-ER fusion product is expressed in the cytoplasm of the transduced cells as an inactive complex with heat shock proteins. After incubation with 4 Hydroxy-Tamoxifen (4HT) the fusion product dissociates and is transported to the nucleus. Indeed, staining of the transduced, ΔNGFR+ B cells with anti-ER antibody in the absence or presence of 4HT illustrates that CASTAT5b localizes as expected in a 4HT dependent manner. Western blot analysis confirmed the presence of the fusion protein of the expected MW in the transduced cells.

The inventor then cultured CASTAT5b-ER-transduced tonsil B cells for 7 days in the absence of 4HT and then added back 4HT. The cells were harvested 24 hr later and tested for expression of BCL-6 by RT-PCR. Expression of BCL-6 transcripts is substantially higher in the culture with 4HT than in the culture without this hormone. To determine whether BCL-6 is a direct or indirect target of STAT5b the protein synthesis inhibitor cycloheximide was added together with 4HT. Upregulation of BCL-6 mRNA was also observed when both 4HT and cycloheximide were added. These data indicate that BCL-6 mRNA expression is directly controlled by STAT5b.

Effect of Constitutive Active Mutants of STAT5 on Growth of Human B Cells

The observation that BCL-6 is a direct of STAT5 proteins in B cells prompted the inventors to investigate whether STAT5 have a similar function as BCL-6 in the regulation of survival, growth and differentiation of B cells. The inventors tested the effects of wild type (WT) and constitutive active (CA) mutants of STAT5 on the growth of human B cells. Tonsillar CD19+ B cells were isolated as indicated in materials and methods. These cells were cocultured with IL-2, IL-4 and mouse fibroblasts transfected with CD40L (CD154). At day 7 the cells were transduced with CA-STAT5a-IRES-GFP, CA-STAT5b-IRES-GFP, WT-STAT5b-IRES-GFP or with a control IRES-GFP. Transduction efficiencies were 5%-20%. The percentages of GFP+ cells in the various cultures didn't change the first three weeks of culture in IL-2, IL-4 and CD40L. However, starting with 21-25 days of culture, the percentage of GFP+ cells in the cultures transduced with CA-STAT5a and b increased over time. At week 6-7 the control-transduced and the untransduced B cells started to die. At week 8 more than 95% of the CA-STAT5b-transduced cultures were GFP+ and continued to expand. B cells transduced with WT STAT5 survived but did not expand indicating that activation of STAT5 is required for expansion of the B cells. The expanded B cells expressed CD19 but lacked CD20. This observation strongly suggested that the replicative life-span extension CA-STAT5-transduced cells was not due to EBV transformation, since EBV transformed B cells express CD20. This was confirmed by the observation that the CA-STAT5b-transduced B cells did not express LMP-1 or EBNA1/2 mRNA as assessed by a sensitive RT-PCR. Importantly the CA-STAT5b-transduced B cells expressed several Ig variable gene segments indicating that the line is not monoclonal.

Generation of B Cell Lines Following Induction of CA-STAT5b Expression with Tamoxifen.

The observation that CA-STAT5b extends the life span of human tonsil B cells could be caused by secondary events resulting in transformation of the cells. If this is the case shutting off STAT5b should not affect the growth of the already transformed B cells. To investigate this the inventor employed the CA-STAT5b-ER-IRES-ΔNGFR construct. Following culture of tonsillar B cells transduced with CASTAT5b-ER IRES-ΔNGFR in CD40L, IL-2 and IL-4 in the presence or absence of 1 µM 4HT a growth selection of CA-STAT5b expressing cells (ΔNGFR+) only occurred in the presence of 4HT. Importantly, removal of 4HT resulted in termination of the growth of the B cells and eventual death. The transduced B cells cultured with CD40L, IL2 and IL-4 cultured in the absence of 4HT initially proliferated, but they ceased to grow and then died after 7-20 days. When 4HT was added back after 7 days, the cells survived and then continued to grow. These results indicate that CA-STAT5b-induced growth of the tonsil B cells is not a consequence of irreversible genetic changes induced by CA-STAT5b transforming the B cells but is only dependent on continued functional expression of CA-STAT5b. The tonsil B cells transduced with CA-STAT5b-ER and cultured in CD40L, IL-2, IL-4 and 4HT express low levels of cell surface IgM with 45% κ and 40% λ chain expression indicating that they are polyclonal. The cells were negative for cell surface IgD and a small percentage (1-2%) expressed IgG an lacked IgM. Furthermore they express CD38, CD40, CD70, CD80 and HLA-DR but are weakly positive for CD20 and negative for CD27. CD25 was highly expressed on these cells consistent with the fact that STAT5b directly controls CD25 (IL-2Rα) transcription [John, 1996; John, 1999].

The finding that cultures of tonsil B cells transduced with CA-STAT5b-ER contained IgM+ B cells and only a few IgG+ B cells might be a consequence of the fact that tonsil B cells are mainly IgM+ cells. However it was also possible that expression of CA-STAT5b leads to selective outgrowth of IgM+ B cells. Therefore the inventor examined the effects of this mutant on growth of IgG+ cells. For these experiments he used peripheral blood B cells of adults. The inventor cultured purified PB B cells, transduced them with CASTAT5b-ER-IRES-GFP. The transduced B cells were then separated in IgM+ and IgG+ cells and cultured further in the presence of 4HT for 35 days. Expression of CASTAT5b-ER-IRES-GFP results in 4HT dependent growth of both IgM and IgG positive B cells. Further analysis of the phenotypes of these cells revealed that the phenotype of the IgG+ cells with respect to expression of CD25, CD38, CD40, CD70, CD80, HLA-DR, CD20 and CD27 was the same as the phenotype of the cultured tonsil B cells.

REFERENCES

Andjelic, S., Hsia, C., Suzuki, H., Kadowaki, T., Koyasu, S., and Liou, H. C. (2000). Phosphatidylinositol 3-kinase and NF-kappa B/Rel are at the divergence of CD40-mediated proliferation and survival pathways. J Immunol 165, 3860-3867.

Ariyoshi, K., Nosaka, T., Yamada, K., Onishi, M., Oka, Y., Miyajima, A., and Kitamura, T. (2000). Constitutive activation of STAT5 by a point mutation in the SH2 domain, *J Biol Chem* 275, 24407-13.

Banchereau, J., de Paoli, P., Valle, A., Garcia, E., and Rousset, F. (1991). Long-term human B cell lines dependent on interleukin-4 and antibody to CD40, *Science* 251, 70-2.

Baron, B. W., Anastasi, J., Thirman, M. J., Furukawa, Y., Fears, S., Kim, D. C., Simone, F., Birkenbach, M., Montag, A., Sadhu, A., et al. (2002). The human programmed cell death-2 (PDCD2) gene is a target of BCL6 repression: Implications for a role of BCL6 in the down-regulation of apoptosis. Proc Natl Acad Sci U S A 99, 2860-2865.

Bonini, C., Ferrari, G., Verzeletti, S., Servida, P., Zappone, E., Ruggieri, L., Ponzoni, M., Rossini, S., Mavilio, F., Traversari, C., and Bordignon, C. (1997). HSV-TK gene transfer into donor lymphocytes for control of allogeneic graft-versus-leukemia. Science 276, 1719-1724.

Chang, C. C., Ye, B. H., Chaganti, R. S., and Dalla-Favera, R. (1996). BCL-6, a POZ/zinc-finger protein, is a sequence-specific transcriptional repressor. Proc Natl Acad Sci U S A 93, 6947-6952.

Dadgostar, H., Zarnegar, B., Hoffmann, A., Qin, X. F., Truong, U., Rao, G., Baltimore, D., and Cheng, G. (2002). Cooperation of multiple signaling pathways in CD40-regulated gene expression in B lymphocytes. Proc Natl Acad Sci U S A 99, 1497-1502.

Dent, A. L., Shaffer, A. L., Yu, X., Allman, D., and Staudt, L. M. (1997). Control of inflammation, cytokine expression, and germinal center formation by BCL-6. Science 276, 589-592.

Fearon, D. T., Manders, P., and Wagner, S. D. (2001). Arrested differentiation, the self-renewing memory lymphocyte, and vaccination. Science 293, 248-250.

Fishwild, D. M., O'Donnell, S. L., Bengoechea, T., Hudson, D. V., Harding, F., Bernhard, S. L., Jones, D., Kay, R. M., Higgins, K. M., Schramm, S. R., and Lonberg, N. (1996). High-avidity human IgG kappa monoclonal antibodies from a novel strain of minilocus transgenic mice, *Nat Biotechnol* 14, 845-51.

Fukuda, T., Yoshida, T., Okada, S., Hatano, M., Miki, T., Ishibashi, K., Okabe, S., Koseki, H., Hirosawa, S., Taniguchi, M., et al. (1997). Disruption of the Bcl6 gene results in an impaired germinal center formation. J Exp Med 186, 439-448.

Gossen, M., Freundlieb, S., Bender, G., Muller, G., Hillen, W., and Bujard, H. (1995). Transcriptional activation by tetracyclines in mammalian cells, Science 268 1766-1769.

Hanenberg, H., Hashino, K., Konishi, H., Hock, R. A., Kato, I., and Williams, D. A. (1997). Optimization of fibronectin-assisted retroviral gene transfer into human CD34+ hematopoietic cells, Hum Gene Ther 8, 2193-206.

Hanenberg, H., Xiao, X. L., Dilloo, D., Hashino, K., Kato, I., and Williams, D. A. (1996). Colocalization of retrovirus and target cells on specific fibronectin fragments increases genetic transduction of mammalian cells, Nat Med 2, 876-82.

Heemskerk, M. H., Blom, B., Nolan, G., Stegmann, A. P., Bakker, A. Q., Weijer, K., Res, P. C., and Spits, H. (1997). Inhibition of T cell and promotion of natural killer cell development by the dominant negative helix loop helix factor Id3, *J Exp Med* 186, 1597-602.

Heemskerk, M. H., Hooijberg, E., Ruizendaal, J. J., van der Weide, M. M., Kueter, E., Bakker, A. Q., Schumacher, T. N., and Spits, H. (1999). Enrichment of an antigen-specific T cell response by retrovirally transduced human dendritic cells, *Cell Immunol* 195, 10-7.

Hoogenboom, H. R., and Chames, P. (2000). Natural and designer binding sites made by phage display technology, *Immunol Today* 21, 371-8.

John, S., Robbins, C. M., and Leonard, W. J. (1996). An IL-2 response element in the human IL-2 receptor alpha chain promoter is a composite element that binds Stat5, Elf-1, HMG-I(Y) and a GATA family protein. Embo J 15, 5627-5635.

John, S., Vinkemeier, U., Soldaini, E., Darnell, J. E., and Leonard, W. J. (1999). The significance of tetramerization in promoter recruitment by Stat5. Mol Cell Biol 19, 1910-1918.

Jones, P. T., Dear, P. H., Foote, J., Neuberger, M. S., and Winter, G. (1986). Replacing the complementarity-determining regions in a human antibody with those from a mouse, Nature 321, 522-5.

Karpas, A., Dremucheva, A., and Czepulkowski, B. H. (2001). A human myeloma cell line suitable for the generation of human monoclonal antibodies, *Proc Natl Acad Sci U S A* 98, 1799-804.

Kinsella, T. M., and Nolan, G. P. (1996). Episomal vectors rapidly and stably produce high-titer recombinant retrovirus., *Human Gene Therapy* 7, 1405-1413.

Lin, Y., Wong, K., and Calame, K. (1997). Repression of c-myc transcription by Blimp-1, an inducer of terminal B cell differentiation. Science 276, 596-599.

Little, M., Kipriyanov, S. M., Le Gall, F., and Moldenhauer, G. (2000). Of mice and men: hybridoma and recombinant antibodies, *Immunol Today* 21, 364-70.

Lord, J. D., McIntosh, B. C., Greenberg, P. D., and Nelson, B. H. (2000). The IL-2 receptor promotes lymphocyte proliferation and induction of the c-myc, bcl-2, and bcl-x genes through the trans-activation domain of Stat5. J Immunol 164, 2533-2541.

Malisan, F., Briere, F., Bridon, J. M., Harindranath, N., Mills, F. C., Max, E. E., Banchereau, J., and Martinez-Valdez, H. (1996). Interleukin-10 induces immunoglobulin G isotype switch recombination in human CD40-activated naive B lymphocytes, *J Exp Med* 183, 937-47.

Mendez, M. J., Green, L. L., Corvalan, J. R., Jia, X. C., Maynard-Currie, C. E., Yang, X. D., Gallo, M. L., Louie, D. M., Lee, D. V., Erickson, K. L., et al. (1997). Functional transplant of megabase human immunoglobulin loci recapitulates human antibody response in mice, *Nat Genet* 15, 146-56.

Moriggl, R., Sexl, V., Piekorz, R., Topham, D., and Ihle, J. N. (1999). Stat5 activation is uniquely associated with cytokine signaling in peripheral T cells, *Immunity* 11, 225-30.

Morrison, S. L., Johnson, M. J., Herzenberg, L. A., and Oi, V. T. (1984). Chimeric human antibody molecules: mouse antigen-binding domains with human constant region domains, *Proc Natl Acad Sci U S A* 81, 6851-5.

Nosaka, T., Kawashima, T., Misawa, K., Ikuta, K., Mui, A. L., and Kitamura, T. (1999). STAT5 as a molecular regulator of proliferation, differentiation and apoptosis in hematopoietic cells. *Embo J* 18, 4754-4765.

Ohashi, K., Miki, T., Hirosawa, S., and Aoki, N. (1995). Characterization of the promoter region of human BCL-6 gene. *Biochem Biophys Res Commun* 214, 461-467.

Onishi, M., Nosaka, T., Misawa, K., Mui, A. L., Gorman, D., McMahon, M., Miyajima, A., and Kitamura, T. (1998). Identification and characterization of a constitutively active STAT5 mutant that promotes cell proliferation, *Mol Cell Biol* 18, 3871-9.

Reljic, R., Wagner, S. D., Peakman, L. J., and Fearon, D. T. (2000). Suppression of signal transducer and activator of transcription 3-dependent B lymphocyte terminal differentiation by BCL-6. *J Exp Med* 192, 1841-1848.

Roder, J. C., Cole, S. P., and Kozbor, D. (1986). The EBV-hybridoma technique, *Methods Enzymol* 121, 140-67.

Sexl, V., Piekorz, R., Moriggl, R., Rohrer, J., Brown, M. P., Bunting, K. D., Rothammer, K., Roussel, M. F., and Ihle, J. N. (2000). Stat5a/b contribute to interleukin 7-induced B-cell precursor expansion, but abl- and bcr/abl-induced transformation are independent of stat5. *Blood* 96, 2277-2283.

Sexl, V., Piekorz, R., Moriggl, R., Rohrer, J., Brown, M. P., Bunting, K. D., Rothammer, K., Roussel, M. F., and Ihle, J. N. (2000). Stat5a/b contribute to interleukin 7-induced B-cell precursor expansion, but abl- and bcr/abl-induced transformation are independent of stat5, *Blood* 96, 2277-83.

Winter, G., Griffiths, A. D., Hawkins, R. E., and Hoogenboom, H. R. (1994). Making antibodies by phage display technology, *Annu Rev Immunol* 12, 433-55.

Shaffer, A. L., Lin, K. I., Kuo, T. C., Yu, X., Hurt, E. M., Rosenwald, A., Giltnane, J. M., Yang, L., Zhao, H., Calame, K., and Staudt, L. M. (2002). Blimp-1 orchestrates plasma cell differentiation by extinguishing the mature B cell gene expression program. Immunity 17, 51-62.

Shaffer, A. L., Yu, X., He, Y., Boldrick, J., Chan, E. P., and Staudt, L. M. (2000). BCL-6 represses genes that function in lymphocyte differentiation, inflammation, and cell cycle control. Immunity 13, 199-212.

Shvarts, A., Brummelkamp, T., Scheeren, F., Koh, E., Daley, G. Q., Spits, H., and Bernards, R. (2002). A senescence rescue screen identifies BCL6 as an inhibitor of anti-proliferative p19ARF-p53 signaling. Genes Dev in press.

Staudt, L. M., Dent, A. L., Shaffer, A. L., and Yu, X. (1999). Regulation of lymphocyte cell fate decisions and lymphomagenesis by BCL-6. Int Rev Immunol 18, 381-403.

Toyama, H., Okada, S., Hatano, M., Takahashi, Y., Takeda, N., Ichii, H., Takemori, T., Kuroda, Y., and Tokuhisa, T. (2002). Memory B cells without somatic hypermutation are generated from Bcl6-deficient B cells. Immunity 17, 329-339.

Turner, C. A., Jr., Mack, D. H., and Davis, M. M. (1994). Blimp-1, a novel zinc finger-containing protein that can drive the maturation of B lymphocytes into immunoglobulin-secreting cells. Cell 77, 297-306.

Vasanwala, F. H., Kusam, S., Toney, L. M., and Dent, A. L. (2002). Repression of AP-1 function: a mechanism for the regulation of Blimp-1 expression and B lymphocyte differentiation by the B cell lymphoma-6 protooncogene. J Immunol 169, 1922-1929.

Ye, B. H., Cattoretti, G., Shen, Q., Zhang, J., Hawe, N., de Waard, R., Leung, C., Nouri-Shirazi, M., Orazi, A., Chaganti, R. S., et al. (1997). The BCL-6 proto-oncogene controls germinal-centre formation and Th2-type inflammation. Nat Genet 16, 161-170.

Ye, B. H., Rao, P. H., Chaganti, R. S., and Dalla-Favera, R. (1993). Cloning of bcl-6, the locus involved in chromosome translocations affecting band 3q27 in B-cell lymphoma. Cancer Res 53, 2732-2735.

TABLE 1

Percentage positive cells

| Antigen | Onset of culture | Week 15 | Week 18 |
|---|---|---|---|
| CD19 | 97 | 85.4 | 93 |
| CD20 | 92.5 | 3 | 1.68 |
| CD27 | 2.5 | 0.5 | 0.27 |
| CD38 | 56 | 43.9 | 22 |
| CD40 | 65 | 96 | 93 |
| CD80 | 8 | 99.7 | 95 |

TABLE 2

Production of IgG (ng/ml)

|  | Exp. 1 | Exp.2 |
|---|---|---|
| caSTAT5b | 996.6(295) | 16.(7.2) |
| clone 43 |  | 40(7.5) |
| clone 47 |  | 15(5.3) |

The invention claimed is:

1. A method of extending the replicative lifespan of primary mature B-cells to produce a stable B-cell line comprising the steps of:
   a) obtaining primary, mature B-cells;
   b) introducing a constitutively active signal transducer of activation and transcription (CA-STAT) protein into said B-cells, expression of said protein in said B cells being effective to extend the replicative life span thereof such that a stable B cell line is produced; and c) maintaining said B-cells of step b) in an environment where they can replicate, wherein said CA-STAT protein is STAT5, STAT5a or STAT5b.

2. A method according to claim 1 wherein the environment comprises any one or more of the IL-2, CD40L and IL-4.

3. A method according to claim 1 wherein the CA-STAT protein is introduced into the cells by transduction.

4. A method according to claim 1, further comprising the step of halting the replication of the cells thereby bringing about terminal differentiation.

5. A method according to claim 4 further comprising the step of extracting an expression product from a terminally differentiated cell.

6. A method according to claim 5 wherein the expression product is a nucleic acid molecule.

7. A method according to claim 6 wherein the expression product is a protein.

8. A method according to claim 5 further comprising producing a pharmaceutical composition comprising the expression product.

9. A method of extending the replicative lifespan of primary B-cells to produce a stable B-cell line comprising the steps of:
a) obtaining primary B-cells;
b) introducing a constitutively active signal transducer of activation and transcription (CA-STAT) protein into said B-cells, expression of said protein in said B cells being effective to extend the replicative life span thereof such that a stable B cell line is produced; and
c) maintaining said B-cells of step b) in an environment where they can replicate, wherein said CA-STAT protein is STAT5, STAT5a or STAT5b wherein said primary B-cells are isolated tonsillar B-cells.

* * * * *